(12) United States Patent
Kuriyama

(10) Patent No.: US 10,264,948 B2
(45) Date of Patent: Apr. 23, 2019

(54) ENDOSCOPE DEVICE

(71) Applicant: OLYMPUS CORPORATION, Tokyo (JP)

(72) Inventor: Naoya Kuriyama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 416 days.

(21) Appl. No.: 15/173,868

(22) Filed: Jun. 6, 2016

(65) Prior Publication Data

US 2016/0278613 A1     Sep. 29, 2016

Related U.S. Application Data

(63) Continuation of application No. PCT/JP2014/074641, filed on Sep. 18, 2014.

(30) Foreign Application Priority Data

Dec. 20, 2013   (JP) .................................. 2013-264121

(51) Int. Cl.
*A61B 1/00* (2006.01)
*A61B 1/06* (2006.01)
(Continued)

(52) U.S. Cl.
CPC .......... *A61B 1/00009* (2013.01); *A61B 1/005* (2013.01); *A61B 1/00114* (2013.01);
(Continued)

(58) Field of Classification Search
CPC ..... A61B 1/00009; A61B 1/0638; A61B 1/05; A61B 1/0646; A61B 1/005; A61B 1/00114
See application file for complete search history.

(56) References Cited

U.S. PATENT DOCUMENTS 6,366,319 B1 * 4/2002 Bills ..................... H04N 9/045
                                                        348/272
2011/0019035 A1   1/2011 Satodate
(Continued)

FOREIGN PATENT DOCUMENTS

JP    S60-089187 A    5/1985
JP    2001-186534 A   7/2001
(Continued)

OTHER PUBLICATIONS

Extended Supplementary European Search Report dated Aug. 25, 2017 in European Patent Application No. 14 87 1004.9.
International Search Report dated Dec. 22, 2014 issued in PCT/JP2014/074641.

*Primary Examiner* — Timothy J Neal
(74) *Attorney, Agent, or Firm* — Scully, Scott, Murphy & Presser, P.C.

(57) ABSTRACT

An endoscope device includes: a light source unit; an imaging device; a color filter in which a filter unit is arranged, the filter unit in which the number of filters which transmit light of a green wavelength band is equal to or larger than half the total number of filters and the number of filters which transmit light of a blue wavelength band is equal to or larger than the number of filters which transmit the light of the green wavelength band; and a noise reducing unit configured to select a pixel of interest based on used filter information determined according to the light emitted by the light source unit and a characteristic of each filter forming the color filter and detect motion between images captured at different times by using an electric signal output by the pixel of interest, thereby reducing a noise component included in the image signal.

3 Claims, 11 Drawing Sheets

(51) Int. Cl.
    *A61B 1/005*      (2006.01)
    *G06T 3/40*      (2006.01)
    *H04N 9/04*      (2006.01)
    *H04N 5/217*      (2011.01)
    *G02B 23/24*      (2006.01)
    *A61B 1/05*      (2006.01)
    *H04N 5/225*      (2006.01)

(52) U.S. Cl.
    CPC ........ *A61B 1/00186* (2013.01); *A61B 1/0638* (2013.01); *A61B 1/0646* (2013.01); *G02B 23/2484* (2013.01); *G06T 3/4015* (2013.01); *H04N 5/217* (2013.01); *H04N 9/045* (2013.01); *A61B 1/05* (2013.01); *H04N 2005/2255* (2013.01); *H04N 2209/043* (2013.01); *H04N 2209/046* (2013.01)

(56) References Cited

U.S. PATENT DOCUMENTS

| | | |
|---|---|---|
| 2011/0176730 A1 | 7/2011 | Sasaki |
| 2011/0228064 A1 | 9/2011 | Sasaki |
| 2011/0317043 A1 | 12/2011 | On |
| 2012/0105612 A1 | 5/2012 | Yoshino |
| 2012/0262559 A1 | 10/2012 | On |

FOREIGN PATENT DOCUMENTS

| | | |
|---|---|---|
| JP | 2005-150903 A | 6/2005 |
| JP | 2011-029722 A | 2/2011 |
| JP | 2011-143100 A | 7/2011 |
| JP | 2011-234844 A | 11/2011 |
| JP | 2012-005512 A | 1/2012 |
| JP | 2012-095828 A | 5/2012 |
| JP | 2012-217579 A | 11/2012 |

\* cited by examiner

FIG.3

| $P_{11}$ | $P_{12}$ | $P_{13}$ | $P_{14}$ | ... |
|---|---|---|---|---|
| $P_{21}$ | $P_{22}$ | $P_{23}$ | $P_{24}$ | ... |
| $P_{31}$ | $P_{32}$ | $P_{33}$ | $P_{34}$ | ... |
| $P_{41}$ | $P_{42}$ | $P_{43}$ | $P_{44}$ | ... |
| ⋮ | ⋮ | ⋮ | ⋮ | ⋱ |

| $B_{11}$ | $G_{12}$ | $B_{13}$ | $G_{14}$ | ... |
|---|---|---|---|---|
| $G_{21}$ | $Mg_{22}$ | $G_{23}$ | $Mg_{24}$ | ... |
| $B_{31}$ | $G_{32}$ | $B_{33}$ | $G_{34}$ | ... |
| $G_{41}$ | $Mg_{42}$ | $G_{43}$ | $Mg_{44}$ | ... |
| ⋮ | ⋮ | ⋮ | ⋮ | ⋱ |

| B₁₁ | Cy₁₂ | B₁₃ | Cy₁₄ | ⋯ |
|---|---|---|---|---|
| Cy₂₁ | R₂₂ | Cy₂₃ | R₂₄ | ⋯ |
| B₃₁ | Cy₃₂ | B₃₃ | Cy₃₄ | ⋯ |
| Cy₄₁ | R₄₂ | Cy₄₃ | R₄₄ | ⋯ |
| ⋮ | ⋮ | ⋮ | ⋮ | ⋱ |

| B₁₁ | Cy₁₂ | B₁₃ | Cy₁₄ | ⋯ |
|---|---|---|---|---|
| Cy₂₁ | Mg₂₂ | Cy₂₃ | Mg₂₄ | ⋯ |
| B₃₁ | Cy₃₂ | B₃₃ | Cy₃₄ | ⋯ |
| Cy₄₁ | Mg₄₂ | Cy₄₃ | Mg₄₄ | ⋯ |
| ⋮ | ⋮ | ⋮ | ⋮ | ⋱ |

| U4 | | | | |
|---|---|---|---|---|
| $B_{11}$ | $Cy_{12}$ | $B_{13}$ | $Cy_{14}$ | ... |
| $Cy_{21}$ | $W_{22}$ | $Cy_{23}$ | $W_{24}$ | ... |
| $B_{31}$ | $Cy_{32}$ | $B_{33}$ | $Cy_{34}$ | ... |
| $Cy_{41}$ | $W_{42}$ | $Cy_{43}$ | $W_{44}$ | ... |
| ⋮ | ⋮ | ⋮ | ⋮ | ⋱ |

| U5 | | | | | | | | |
|---|---|---|---|---|---|---|---|---|
| $B_{11}$ | $G_{12}$ | $Mg_{13}$ | $G_{14}$ | $B_{15}$ | $G_{16}$ | $Mg_{17}$ | $G_{18}$ | ... |
| $G_{21}$ | $Mg_{22}$ | $G_{23}$ | $B_{24}$ | $G_{25}$ | $Mg_{26}$ | $G_{27}$ | $B_{28}$ | ... |
| $Mg_{31}$ | $G_{32}$ | $B_{33}$ | $G_{34}$ | $Mg_{35}$ | $G_{36}$ | $B_{37}$ | $G_{38}$ | ... |
| $G_{41}$ | $B_{42}$ | $G_{43}$ | $Mg_{44}$ | $G_{45}$ | $B_{46}$ | $G_{47}$ | $Mg_{48}$ | ... |
| $B_{51}$ | $G_{52}$ | $Mg_{53}$ | $G_{54}$ | $B_{55}$ | $G_{56}$ | $Mg_{57}$ | $G_{58}$ | ... |
| $G_{61}$ | $Mg_{62}$ | $G_{63}$ | $B_{64}$ | $G_{65}$ | $Mg_{66}$ | $G_{67}$ | $B_{68}$ | ... |
| $Mg_{71}$ | $G_{72}$ | $B_{73}$ | $G_{74}$ | $Mg_{75}$ | $G_{76}$ | $B_{77}$ | $G_{78}$ | ... |
| $G_{81}$ | $B_{82}$ | $G_{83}$ | $Mg_{84}$ | $G_{85}$ | $B_{86}$ | $G_{87}$ | $Mg_{88}$ | ... |
| ⋮ | ⋮ | ⋮ | ⋮ | ⋮ | ⋮ | ⋮ | ⋮ | ⋱ |

FIG.10

|   |   |   |   |   |   |   |   |   |
|---|---|---|---|---|---|---|---|---|
| $B_{11}$ | $W_{12}$ | $Mg_{13}$ | $W_{14}$ | $B_{15}$ | $W_{16}$ | $Mg_{17}$ | $W_{18}$ | ... |
| $W_{21}$ | $Mg_{22}$ | $W_{23}$ | $B_{24}$ | $W_{25}$ | $Mg_{26}$ | $W_{27}$ | $B_{28}$ | ... |
| $Mg_{31}$ | $W_{32}$ | $B_{33}$ | $W_{34}$ | $Mg_{35}$ | $W_{36}$ | $B_{37}$ | $W_{38}$ | ... |
| $W_{41}$ | $B_{42}$ | $W_{43}$ | $Mg_{44}$ | $W_{45}$ | $B_{46}$ | $W_{47}$ | $Mg_{48}$ | ... |
| $B_{51}$ | $W_{52}$ | $Mg_{53}$ | $W_{54}$ | $B_{55}$ | $W_{56}$ | $Mg_{57}$ | $W_{58}$ | ... |
| $W_{61}$ | $Mg_{62}$ | $W_{63}$ | $B_{64}$ | $W_{65}$ | $Mg_{66}$ | $W_{67}$ | $B_{68}$ | ... |
| $Mg_{71}$ | $W_{72}$ | $B_{73}$ | $W_{74}$ | $Mg_{75}$ | $W_{76}$ | $B_{77}$ | $W_{78}$ | ... |
| $W_{81}$ | $B_{82}$ | $W_{83}$ | $Mg_{84}$ | $W_{85}$ | $B_{86}$ | $W_{87}$ | $Mg_{88}$ | ... |
| ⋮ | ⋮ | ⋮ | ⋮ | ⋮ | ⋮ | ⋮ | ⋮ | ⋱ |

FIG.11

| COLOR FILTER TYPE | ILLUMINATION LIGHT | |
|---|---|---|
| | WHITE LIGHT | NARROW BAND LIGHT |
| COLOR FILTER 202a_1 | G | B,Mg |
| COLOR FILTER 202a_2 | Cy | Cy |
| COLOR FILTER 202a_3 | Cy | Cy |
| COLOR FILTER 202a_4 | Cy | Cy,W |
| COLOR FILTER 202a_5 | G | B,Mg |
| COLOR FILTER 202a_6 | W | W |

ENDOSCOPE DEVICE

CROSS-REFERENCE TO RELATED APPLICATIONS

This application is a continuation of PCT international application Ser. No. PCT/JP2014/074641 filed on Sep. 18, 2014 which designates the United States, incorporated herein by reference, and which claims the benefit of priority from Japanese Patent Applications No. 2013-264121, filed on Dec. 20, 2013, incorporated herein by reference.

BACKGROUND

1. Field of the Disclosure

The present disclosure relates to an endoscope device introduced into a living body to obtain an in-vivo image.

2. Description of the Related Art

Technology of detecting a motion amount between frames based on a current frame and a previous frame corresponding to image signals temporally adjacent to each other generated by an imaging device to reduce a noise component of the current frame according to the motion amount is conventionally known as noise reduction processing (hereinafter, referred to as "NR processing)) of reducing the noise component included in the image signal generated by the imaging device such as a CCD (charge coupled device) and a CMOS (complementary metal oxide semiconductor) (see Japanese Patent Application Laid-open No. 2005-150903).

Technology of detecting the motion amount between the frames based on a pixel value of a pixel which receives light transmitted through a filter which transmits a specific color component out of the image signal generated by the imaging device to reduce the noise component of the current frame according to the motion amount is known as another NR processing (see Japanese Patent Application Laid-open No. 2011-029722).

Recently, the endoscope device uses a narrow band imaging (NBI) system in which illumination light formed of two types of narrow band light included in blue and green light wavelength bands (hereinafter, referred to as "narrow band illumination light") is used for observing a capillary, a mucosal fine pattern and the like on a mucous membrane surface of the living body in addition to white light imaging (WLI) system in which white illumination light (hereinafter referred to as "white illumination light") is used.

However, when the above-described white illumination light imaging system and narrow band imaging system are performed, when the NR processing is performed based on the pixel value output from the pixel on which a specific filter is provided, the pixel value of each pixel differs depending on different characteristics of the imaging system, so that there is a problem that the noise component may be appropriately reduced in one imaging system but the noise component may not be appropriately reduced in the other imaging system.

There is a need for an endoscope device capable of appropriately reducing the noise component in both the white illumination light imaging system and the narrow band imaging system.

SUMMARY

According to one aspect of the present disclosure, there is provided an endoscope device according to the present disclosure includes: a light source unit configured to emit white illumination light including light of red, green and blue wavelength bands or narrow band illumination light formed of narrow band light included in each of the blue and green wavelength bands; an imaging device configured to perform photoelectric conversion on light received by a plurality of pixels arranged in a lattice pattern to generate an electric signal as an image signal; a color filter in which a filter unit is arranged so as to correspond to the plurality of pixels, the filter unit formed of a plurality of filters including at least a filter which transmits the light of the blue wavelength band and a filter which transmits the light of the blue wavelength band and the light of at least one of the green and red wavelength bands in which the number of filters which transmit the light of the green wavelength band is equal to or larger than half the total number of filters of the filter unit and the number of filters which transmit the light of the blue wavelength band is equal to or larger than the number of filters which transmit the light of the green wavelength band; and a noise reducing unit configured to select a pixel of interest based on used filter information determined according to the light emitted by the light source unit and a characteristic of each filter forming the color filter and detect motion between images captured at different times by using the electric signal output by the pixel of interest, thereby reducing a noise component included in the image signal.

The above and other objects, features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 3 is a schematic diagram illustrating a configuration of a pixel of an imaging device of the endoscope device according to one embodiment of the present disclosure;

FIG. 4 is a schematic diagram illustrating an example of a configuration of a color filter of the endoscope device according to one embodiment of the present disclosure;

FIG. 6 is a schematic diagram illustrating another example of the configuration of the color filter according to one embodiment of the present disclosure;

FIG. 7 is a schematic diagram illustrating another example of the configuration of the color filter according to one embodiment of the present disclosure;

FIG. 8 is a schematic diagram illustrating another example of the configuration of the color filter according to one embodiment of the present disclosure;

FIG. 9 is a schematic diagram illustrating another example of the configuration of the color filter according to one embodiment of the present disclosure;

FIG. 10 is a schematic diagram illustrating another example of the configuration of the color filter according to one embodiment of the present disclosure;

FIG. 11 is a view illustrating an example of used filter information recorded by a used filter information recording unit of the endoscope device according to one embodiment of the present disclosure;

DETAILED DESCRIPTION OF THE PREFERRED EMBODIMENTS

Figure 1:
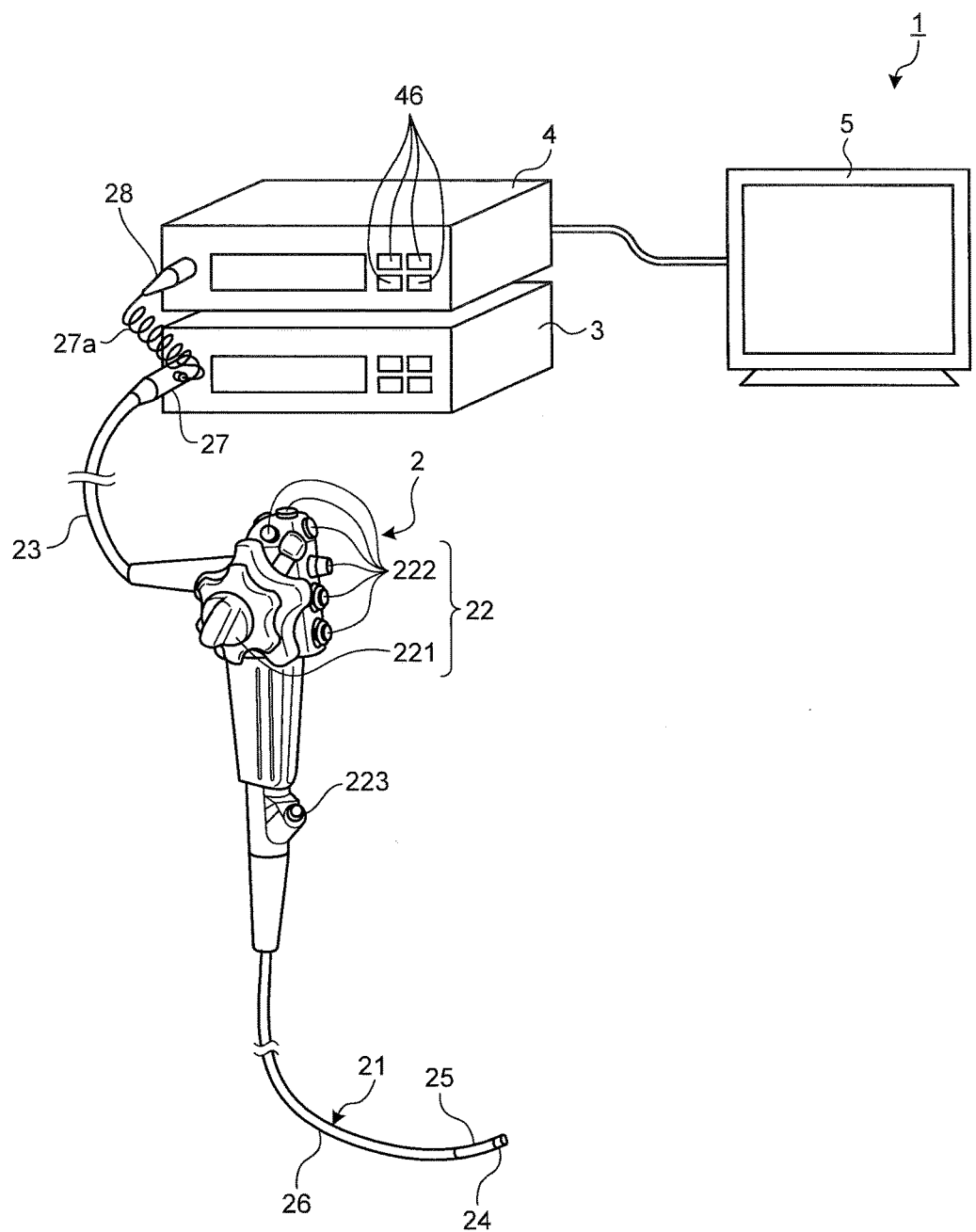
FIG. 1 is a view illustrating a schematic configuration of an endoscope device according to one embodiment of the present disclosure.

A mode for carrying out the present disclosure (hereinafter, referred to as an "embodiment") is hereinafter described. A medical endoscope device which captures an image in a body cavity of a subject such as a patient to display is described in the embodiment. The present disclosure is not limited by the embodiment. In the drawings, the same part is described with the same reference numeral assigned.

Figure 2:
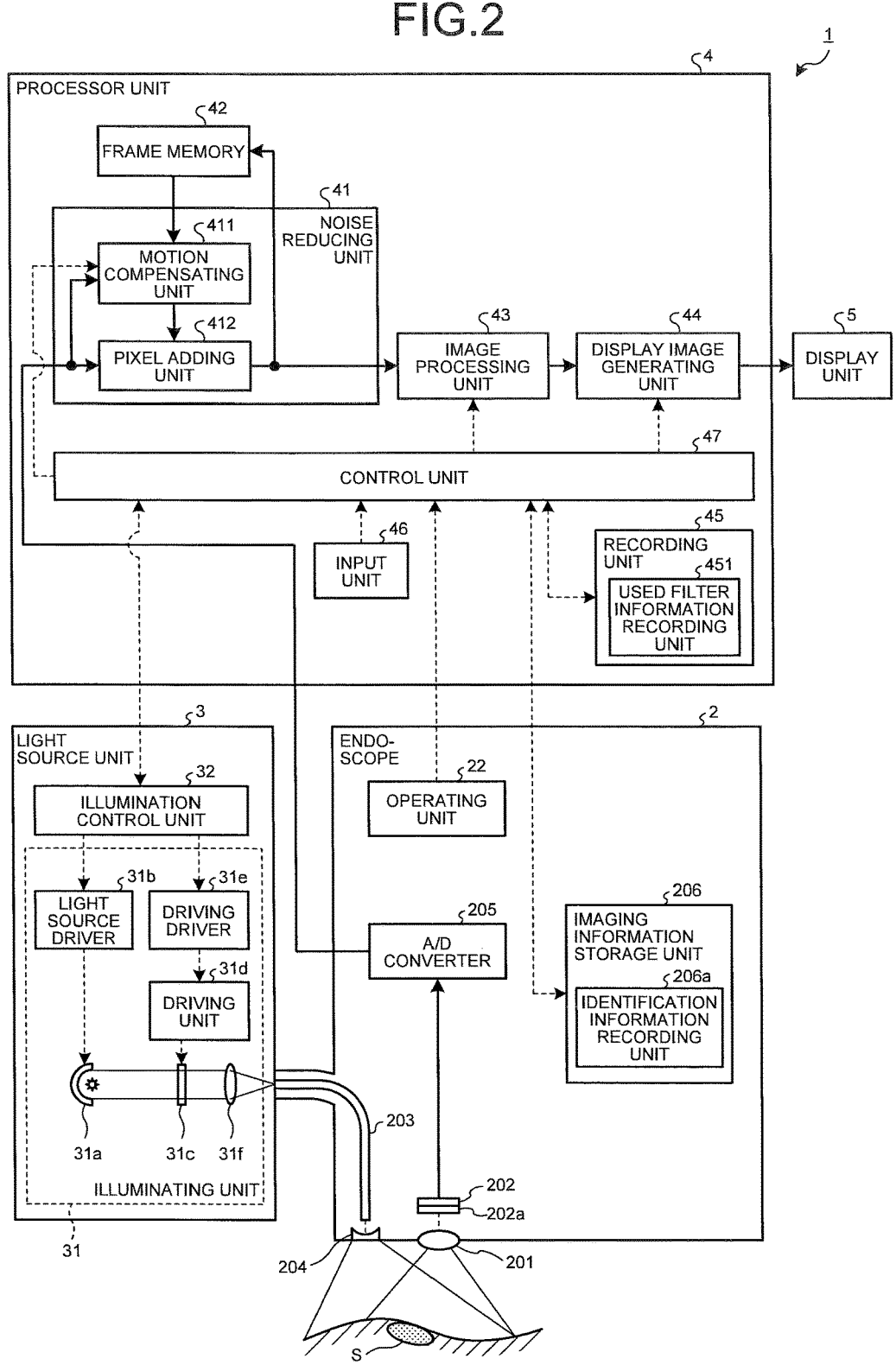
FIG. 2 is a schematic diagram illustrating the schematic configuration of the endoscope device according to one embodiment of the present disclosure.

FIG. 1 is a view illustrating a schematic configuration of the endoscope device according to one embodiment of the present disclosure. FIG. 2 is a schematic diagram illustrating the schematic configuration of the endoscope device according to one embodiment of the present disclosure.

An endoscope device 1 illustrated in FIGS. 1 and 2 is provided with an endoscope 2 (endoscope) which image an observed region in the subject with a distal end inserted in the body cavity of the subject, thereby generating an in-vivo image (image signal) of the observed region, a light source unit 3 (light source device) which emits white illumination light including light of red, green, and blue wavelength bands or narrow band illumination light formed of narrow band light included in each of the above-described blue and green wavelength bands from the distal end of the endoscope 2 toward the observed region through the endoscope 2, a processor unit 4 (processing device) which applies predetermined imaging processing on the in-vivo image generated by an imaging device 202 and generally controls operation of an entire endoscope device 1, and a display unit 5 which displays the in-vivo image on which the processor unit 4 applies the image processing. The endoscope device 1 obtains the in-vivo image in the body cavity with an insertion part 21 inserted in the body cavity of the subject such as the patient. A user such as a doctor observes the obtained in-vivo image to examine whether there is a bleeding site and a tumor site (lesion S) being sites to be detected.

A configuration of the endoscope 2 is first described.

The endoscope 2 is provided with a flexible insertion part 21 having an elongated shape, an operating unit 22 connected to a proximal end side of the insertion part 21 to accept an input of various operating signals, and a universal code 23 extending in a direction different from a direction in which the insertion part 21 extends from the operating unit 22 in which various cables connected to the light source unit 3 and the processor unit 4 are embedded.

The insertion part 21 includes a distal end 24 in which the imaging device 202 including pixels (photo diodes) which receive light arranged in a lattice (matrix) pattern which generates the image signal by performing photoelectric conversion on the light received by the pixels is embedded, a bending part 25 freely bendable formed of a plurality of bending pieces, and an elongated flexible tube part 26 having flexibility connected to a proximal end side of the bending part 25.

The operating unit 22 includes a bending knob 221 which bends the bending part 25 upward/downward and rightward/leftward and a plurality of switches 222 being an operation input unit which inputs operation instruction signals of peripheral devices such as air supply means, water supply means, and gas supply means in addition to the light source unit 3 and the processor unit 4 (see FIG. 1). The operating unit 22 also includes a treatment tool insertion part 223 from which a treatment tool such as in-vivo forceps, a laser scalpel, and an inspection probe is inserted in the body cavity; the treatment tool inserted from the treatment tool insertion part 223 is exposed from an aperture (not illustrated) through a treatment tool channel (not illustrated) of the distal end 24.

The universal code 23 includes at least a light guide 203 and a cable assembly formed of one cable of a plurality of assembled cables embedded therein. The cable assembly being a signal line which transmits and receives a signal between the endoscope 2 and the light source unit 3 and processor unit 4 includes a signal line for transmitting and receiving setting data, a signal line for transmitting and receiving the image signal, a signal line for transmitting and receiving a driving timing signal for driving the imaging device 202 and the like. The universal code 23 includes a connector unit 27 detachably attached to the light source unit 3. The connector unit 27 from which a coil-shaped coil cable 27a extends includes a connector unit 28 detachably attached to the processor unit 4 on an extended end of the coil cable 27a.

The endoscope 2 is at least provided with an imaging optical system 201, the imaging device 202, the light guide 203, a lens for illumination 204, an A/D converter 205, and an imaging information storage unit 206.

The imaging optical system 201 provided at the distal end of the endoscope 2 condenses at least the light from the observed region. The imaging optical system 201 is formed of one or a plurality of lenses. Meanwhile, the imaging optical system 201 may also be provided with an optical zooming mechanism which changes an angle of view and a focusing mechanism which changes a focal point.

The imaging device 202 provided so as to be perpendicular to an optical axis of the imaging optical system 201 performs the photoelectric conversion on an image of the light formed by the imaging optical system 201 to generate an electric signal (image signal). The imaging device 202 is realized by using a CCD (charge coupled device) image sensor and a CMOS (complementary metal oxide semiconductor) image sensor.

Here, a configuration of the pixel of the imaging device 202 is described. FIG. 3 is a schematic diagram illustrating the configuration of the pixel of the imaging device 202.

As illustrated in FIG. 3, the imaging device 202 includes a plurality of pixels which receives the light from the imaging optical system 201 arranged in a lattice (matrix) pattern. The imaging device 202 performs the photoelectric conversion on the light received by each pixel to generate the electric signal (also referred to as the image signal, a pixel value and the like) as the image signal. The electric signal includes the pixel value (luminance value), positional information of the pixel and the like. In FIG. 3, the pixel arranged on i-th row j-th column is represented as a pixel $P_{ij}$.

The imaging device 202 is provided with a color filter 202a including a plurality of filters each of which transmits the light of an individually set wavelength band arranged between the imaging optical system 201 and the imaging device 202. The color filter 202a is provided on a light receiving surface of the imaging device 202.

Here, a configuration of the color filter 202a is described. In this embodiment, a plurality of types of color filters 202a may be used. Therefore, the configuration of the color filter 202a applicable to this embodiment is hereinafter described.

Configuration 1 of Color Filter

FIG. 4 is a schematic diagram illustrating an example of the configuration (configuration 1) of the color filter 202a.

A color filter 202a_1 illustrated in FIG. 4 is such that filter units U1 each of which is formed of four filters arranged in a 2×2 matrix pattern, for example, are arranged in a two-dimensional manner (matrix pattern) according to arrangement of the pixels $P_{ij}$ in this embodiment. The pixel $P_{ij}$ on which the filter is provided receives the light of the wavelength band which the filter transmits. For example, the pixel $P_{ij}$ on which the filter which transmits the light of the blue wavelength band is provided receives the light of the blue wavelength band. Hereinafter, the pixel $P_{ij}$ which receives the light of the blue wavelength band is referred to as a B pixel. Similarly, the pixel $P_{ij}$ which receives the light of the green wavelength band is referred to as a G pixel, and the pixel $P_{ij}$ which receives the light of the red wavelength band is referred to as an R pixel.

Here, the filter unit U1 transmits the light of a blue (B) wavelength band $H_B$, a green (G) wavelength band $H_G$, and a red (R) wavelength band $H_R$. In addition, in the filter unit U1, a plurality of filters is selected to be arranged such that the number of filters which transmit the light of the wavelength band $H_G$ is equal to or larger than half the total number of filters forming the filter unit U1 and the number of filters which transmit the light of the wavelength band $H_B$ is equal to or larger than the number of filters which transmit the light of the wavelength band $H_G$. The blue, green, and red wavelength bands $H_B$, $H_G$, and $H_R$ are such that the wavelength band $H_B$ is 390 nm to 500 nm, the wavelength band $H_G$ is 500 nm to 600 nm, and the wavelength band $H_R$ is 600 nm to 700 nm, for example.

As illustrated in FIG. 4, the filter unit U1 according to this embodiment is formed of one B filter which transmits the light of the wavelength band $H_B$, two G filters which transmit the light of the wavelength band $H_G$, and one Mg filter which transmits the light of the wavelength bands $H_B$ and $H_R$. Hereinafter, when the B filter is provided in a position corresponding to the pixel $P_{ij}$, the B filter is represented as $B_{ij}$. Similarly, when the G filter is provided in a position corresponding to the pixel $P_{ij}$, the G filter is represented as $G_{ij}$, and when the Mg filter is provided in a position corresponding to the pixel $P_{ij}$, the Mg filter is represented as $Mg_{ij}$.

The filter unit U1 includes two filters which transmit the light of the wavelength band $H_G$ (G filters) and two filters which transmit the light of the wavelength band $H_B$ (B filter and Mg filter).

Figure 5:
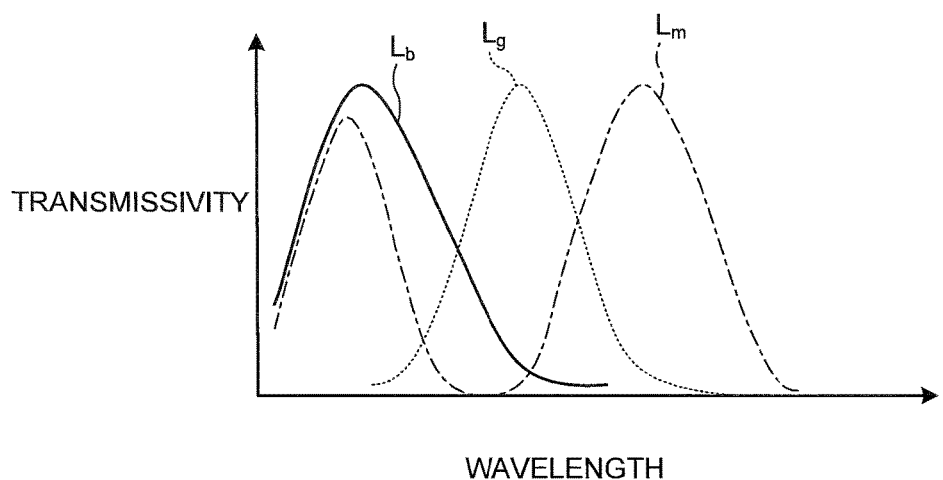
FIG. 5 is a view illustrating an example of a characteristic of each filter of the color filter according to one embodiment of the present disclosure.

FIG. 5 is a view illustrating an example of a characteristic of each filter of the color filter 202a _1 according to this embodiment, the view illustrating relationship between a wavelength of the light and transmissivity of each filter. In FIG. 5, a transmissivity curve is standardized such that maximum values of the transmissivity of respective filters are the same. A curve $L_b$ (solid line), a curve $L_g$ (broken line), and a curve $L_m$ (dashed line) illustrated in FIG. 5 indicate the transmissivity curves of the B filter, the G filter, and the Mg filter, respectively.

As illustrated in FIG. 5, the B filter transmits the light of the wavelength band $H_B$. The Mg filter transmits the light of a wavelength band of magenta being a complementary color of green. In other words, the Mg filter absorbs the light of the wavelength band $H_G$ and transmits the light of the wavelength bands $H_B$ and $H_R$. The G filter transmits the light of the wavelength band $H_G$. Meanwhile, in this specification, the complementary color refers to the color formed of the light including at least two wavelength bands out of the wavelength bands $H_B$, $H_G$, and $H_R$.

Configuration 2 of Color Filter

FIG. 6 is a schematic diagram illustrating another example of the configuration (configuration 2) of the color filter 202a according to this embodiment.

A color filter 202a_2 illustrated in FIG. 6 is such that filter units U2 each of which is formed of four filters arranged in a 2×2 lattice pattern, for example, are arranged in a two-dimensional manner in this embodiment. The filter unit U2 is formed of one B filter which transmits the light of the wavelength band $H_B$, two Cy filters which transmit the light of the wavelength bands $H_B$ and $H_G$, and one R filter which transmits the light of the wavelength band $H_R$.

The Cy filter transmits the light of a wavelength band of cyan being a complementary color of red. In other words, the Cy filter absorbs the light of the wavelength band $H_R$ and transmits the light of the wavelength bands $H_B$ and $H_G$.

The filter unit U2 includes two filters which transmit the light of the wavelength band $H_G$ (Cy filters) and three filters which transmit the light of the wavelength band $H_B$ (B filter and Cy filters).

Configuration 3 of Color Filter

FIG. 7 is a schematic diagram illustrating another example of the configuration (configuration 3) of the color filter 202a according to this embodiment.

A color filter 202a_3 illustrated in FIG. 7 is such that filter units U3 each of which is formed of four filters arranged in a 2×2 lattice pattern, for example, are arranged in a two-dimensional manner in this embodiment. The filter unit U3 is formed of one B filter which transmits the light of the wavelength band $H_B$, two Cy filters which transmit the light of the wavelength bands $H_B$ and $H_G$, and one Mg filter which transmits the light of the wavelength bands $H_B$ and $H_R$.

The filter unit U3 includes two filters which transmit the light of the wavelength band $H_G$ (Cy filters) and four filters which transmit the light of the wavelength band $H_B$ (B filter, Cy filters, and Mg filter).

Configuration 4 of Color Filter

FIG. 8 is a schematic diagram illustrating another example of the configuration (configuration 4) of the color filter 202a according to this embodiment.

A color filter 202a_4 illustrated in FIG. 8 is such that filter units U4 each of which is formed of four filters arranged in a 2×2 lattice pattern, for example, are arranged in a two-dimensional manner in this embodiment. The filter unit U4 is formed of one B filter which transmits the light of the wavelength band $H_B$, two Cy filters which transmit the light of the wavelength bands $H_B$ and $H_G$, and one W filter which transmits the light of the wavelength bands $H_B$, $H_G$, and $H_R$.

The W filter transmits the light of a white wavelength band. In other words, the W filter transmits the light of the wavelength bands $H_B$, $H_G$, and $H_R$ (white light). Meanwhile, it is also possible not to provide the W filter but make this region a vacant (transparent) filter region.

The filter unit U4 includes three filters which transmit the light of the wavelength band $H_G$ (Cy filters and W filter) and four filters which transmit the light of the wavelength band $H_B$ (B filter, Cy filters, and W filter).

Configuration 5 of Color Filter

FIG. 9 is a schematic diagram illustrating another example of the configuration (configuration 5) of the color filter 202a according to this embodiment.

A color filter 202a_5 illustrated in FIG. 9 is such that filter units U5 each of which is formed of 16 filters arranged in a 4×4 matrix pattern, for example, are arranged in a two-dimensional manner in this embodiment. The filter unit U5 includes a plurality of the above-described B filters, G filters, and Mg filters in which the G filters are arranged on an orthogonal line.

The filter unit U5 includes eight filters which transmit the light of the wavelength band $H_G$ (G filters) and eight filters which transmit the light of the wavelength band $H_B$ (B filters and Mg filters).

Configuration 6 of Color Filter

FIG. 10 is a schematic diagram illustrating another example of the configuration (configuration 6) of the color filter according to this embodiment.

A color filter 202a_6 illustrated in FIG. 10 is such that filter units U6 each of which is formed of 16 filters arranged in a 4×4 lattice pattern, for example, are arranged in a two-dimensional manner in this embodiment. The filter unit U6 includes a plurality of the above-described B filters, Mg filters, and W filters in which the W filters are arranged on an orthogonal line.

The filter unit U6 includes eight filters which transmit the light of the wavelength band $H_G$ (W filters) and 16 filters which transmit the light of the wavelength band $H_B$ (B filters, Mg filters, and W filters).

In this manner, any one of the above-described six types of color filters 202a is provided on the light receiving surface of the imaging device 202 in this embodiment. Any color filter in which the number of filters which transmit the light of the wavelength band $H_G$ is equal to or larger than half the number of filters which form the filter unit and the number of filters which transmit the light of the wavelength band $H_B$ is equal to or larger than the number of filters which transmit the light of the wavelength band $H_G$ in the filter unit may serve as the color filter 202a according to the above-described embodiment; arrangement satisfying the above-described condition is also applicable in addition to the above-described arrangement. Meanwhile, hereinafter, the pixel $P_{ij}$ which receives the light of the wavelength band $H_G$, the pixel $P_{ij}$ which receives the light of the wavelength band $H_R$, the pixel $P_{ij}$ which receives the light of the wavelength bands $H_B$ and $H_G$, the pixel $P_{ij}$ which receives the light of the wavelength band $H_B$ and $H_R$, and the pixel $P_{ij}$ which receives the light of the wavelength bands $H_B$, $H_G$, and $H_R$ are described as the G pixel, the R pixel, the Cy pixel, the Mg pixel, and the W pixel, respectively.

With reference to FIGS. 1 and 2 again, the configuration of the endoscope 2 is continuously described.

The light guide 203 formed of a glass fiber and the like serves as a light guide path of the light emitted from the light source unit 3.

The lens for illumination 204 provided at a distal end of the light guide 203 diffuses the light guided by the light guide 203 to emit from the distal end 24 to outside.

The A/D converter 205 A/D converts the image signal generated by the imaging device 202 and outputs digital-converted image signal (electric signal) to the processor unit 4.

The imaging information storage unit 206 stores data including various programs for operating the endoscope 2, various parameters required for operating the endoscope 2, identification information D of the endoscope 2 and the like. The identification information D includes a scope ID being specific information (ID) of the endoscope 2, a model year, specification information, a transmission system, a transmission rate, arrangement information of the transmission filters regarding the color filter 202a associated with the scope ID and the like. The imaging information storage unit 206 is realized by using a semiconductor memory such as a flash memory.

Next, a configuration of the light source unit 3 is described.

The light source unit 3 is provided with an illuminating unit 31 and an illumination control unit 32.

The illuminating unit 31 switches between a plurality of types of illumination light of different wavelength bands to emit under the control of the illumination control unit 32. The illuminating unit 31 switches between a plurality of types of illumination light of different wavelength bands to emit. The illuminating unit 31 includes a light source 31a, a light source driver 31b, a switching filter 31c, a driving unit 31d, a driving driver 31e, and a condenser lens 31f.

The light source 31a emits the white illumination light including the light of the red, green, and blue wavelength bands $H_R$, $H_G$, and $H_B$ under the control of the illumination control unit 32. The white illumination light emitted by the light source 31a is emitted from the distal end 24 to outside through the switching filter 31c, the condenser lens 31f, and the light guide 203. The light source 31a is realized by using the light source which emits the white light such as a white LED and a xenon lamp.

The light source driver 31b supplies the light source 31a with current to allow the light source 31a to emit the white illumination light under the control of the illumination control unit 32.

The switching filter 31c transmits only the blue narrow band light and the green narrow band light out of the white illumination light emitted by the light source 31a. The switching filter 31c is removably put on an optical path of the white illumination light emitted by the light source 31a under the control of the illumination control unit 32. The switching filter 31c is put on the optical path of the white illumination light to transmit only the two types of narrow band light. Specifically, the switching filter 31c transmits the narrow band illumination light formed of light of a narrow band $T_B$ included in the wavelength band $H_B$ (for example, 390 nm to 445 nm) and light of a narrow band $T_G$ included in the wavelength band $H_G$ (for example, 530 nm to 550 nm). The narrow bands $T_B$ and $T_G$ are the wavelength bands of blue light and green light easily absorbed by hemoglobin in blood. Light limited to the band to be emitted is referred to as the narrow band illumination light and observation of the image by using the narrow band illumination light is referred to as a narrow band imaging (NBI) system.

The driving unit 31d puts/removes the switching filter 31c on/from the optical path of the light source 31a. The driving unit 31d is formed of a stepping motor, a DC motor and the like.

The driving driver 31e supplies the driving unit 31d with predetermined current under the control of the illumination control unit 32.

The condenser lens 31f condenses the white illumination light emitted by the light source 31a or the narrow band illumination light transmitted through the switching filter 31c to emit out of the light source unit 3 (light guide 203).

The illumination control unit 32 controls the light source driver 31b to turn on/off the light source 31a. The illumination control unit 32 controls the type (band) of the illumination light emitted by the illuminating unit 31 by putting/removing the switching filter 31c on/from the optical path of the light source 31a by controlling the driving driver 31e. Specifically, the illumination control unit 32 controls to switch the illumination light emitted by the illuminating unit 31 to the white illumination light or the narrow band illumination light by putting/removing the switching filter 31c on/from the optical path of the light source 31a. In other words, the illumination control unit 32 controls to switch to a white light imaging (WLI) system in which the white illumination light including the light of the wavelength bands $H_B$, $H_G$, and $H_R$ is used or the narrow band imaging (NBI) system in which the narrow band illumination light formed of the light of the narrow bands $T_B$ and $T_G$ is used.

Next, a configuration of the processor unit 4 is described.

The processor unit 4 is provided with a noise reducing unit 41, a frame memory 42, an image processing unit 43, a display image generating unit 44, a recording unit 45, an input unit 46, and a control unit 47.

The noise reducing unit 41 performs NR processing of reducing a noise component included in the image signal input from the A/D converter 205 to output to the image processing unit 43 and the frame memory 42. The noise reducing unit 41 includes a motion compensating unit 411 and a pixel adding unit 412.

The motion compensating unit 411 selects a pixel of interest based on used filter information determined according to the light emitted by the light source unit 3 and the characteristic of each filter forming the color filter 202a recorded in a used filter information recording unit 451 to be described later and detects motion between the images which the imaging device 202 captures at different times to generate by using the electric signal (pixel value) output by the pixel of interest, thereby reducing the noise component included in the image signal generated by the imaging device 202. Specifically, the motion compensating unit 411 performs motion compensating processing of compensating motion between two images (frames) corresponding to the image signals temporally adjacent to each other generated by the imaging device 202.

The pixel adding unit 412 adds the pixel value of each pixel of a previous frame (compensated image) corresponding to the image signal on which the motion compensation of the image is performed input from the motion compensating unit 411 to the pixel value (electric signal) of each pixel of a current frame (latest frame) corresponding to a latest image signal input from the A/D converter 205 or takes an average of them, thereby reducing the noise component included in the current frame (latest image) corresponding to the image signal of the latest image and outputs the current frame (latest image) corresponding to the image signal from which the noise component is reduced to the frame memory 42 and the image processing unit 43.

The frame memory 42 stores the image signal (current frame) from which the noise component is reduced input from the noise reducing unit 41. The frame memory 42 is formed of a semiconductor memory such as an SDRAM.

The image processing unit 43 performs various types of image processing on the current frame (latest image) corresponding to the latest image signal input from the noise reducing unit 41 to output to the display image generating unit 44. Here, the image processing performed by the image processing unit 43 includes OB clamping processing of correcting an offset amount of a black level, demosaicing processing of interpolating a lacking color component based on a correlation value of color information of a plurality of pixels, and gain adjusting processing of performing gradation processing of a brightness level and color image generating processing of generating a color image signal of the image signal on which the demosaicing processing is applied.

The display image generating unit 44 performs gradation converting processing, enlarging processing and/or structure emphasis processing of a capillary, a mucosal fine pattern or the like on a mucous membrane surface on the current frame (latest image) corresponding to the image signal of the latest image input from the image processing unit 43 to output to the display unit 5.

The recording unit 45 records data including various programs for operating the endoscope device 1, various parameters required for operating the endoscope device 1 and the like. The recording unit 45 is realized by using a semiconductor memory such as a flash memory and an SDRAM. The recording unit 45 includes the used filter information recording unit 451.

The used filter information recording unit 451 records the used filter information regarding the filter used when the motion compensating unit 411 performs the motion compensation on the image signal generated by the imaging device 202.

FIG. 11 is a view illustrating an example of the used filter information which the used filter information recording unit 451 records. Used filter information T1 illustrated in FIG. 11 records the type of filter used by the motion compensating unit 411 in the motion compensating processing according to the type of illumination light for each color filter. Although the color filter 202a provided on the imaging device 202 is basically fixed and may not be changed, the endoscope 2 (scope) itself may be changed in this embodiment. Therefore, "type of color filter" is associated with "used filter information T1" illustrated in FIG. 11 to be managed as the "scope ID" in actual usage; however, this is represented herein as "color filter type" for making the description simple. Under this precondition, conditions when the motion compensating unit 411 sets the filter used in the motion compensating processing is described. When the motion compensating unit 411 sets the filter used in the motion compensating processing, this first sets the filter based on condition 1 out of following two conditions 1 and 2, and when there is a plurality of candidates with condition 1, this narrows the candidates to set the used filter based on condition 2:

condition 1: filter of the greatest number of filters which transmit the same type of color component in the filter unit, and condition 2: when there is a plurality of filters satisfying condition 1, the filter having higher sensitivity to the narrow band illumination light. Here, order of sensitivity is as follows: W filter>Cy filter>B filter>Mg filter>G filter.

Meanwhile, it is sufficient to consider conditions 1 and 2 for the filter units U1 to U6 forming the color filters 202a_1 to 202a_6, respectively.

First, the color filter 202a_1 is described. When the illumination light is the white light, the G filter serves as the filter for the motion compensating processing based on condition 1. When the illumination light is the narrow band light, the Mg filter transmits only the light of the wavelength band $H_B$, so that this is substantially regarded as the B filter. Therefore, based on condition 1, the number of filters which transmit the light of the wavelength band $H_B$ and the number of filters which transmit the light of the wavelength band $H_G$ are the same. Then, condition 2 is applied and the B filter (including the Mg filter) serves as the filter for the motion compensating processing because the B filter has higher sensitivity than the G filter.

The color filter 202a_2 is described. When the illumination light is the white light, the Cy filter serves as the filter for the motion compensating processing based on condition 1. When the illumination light is the narrow band light, since the Cy filter directly transmits a cyan color component, so that the Cy filter serves as the filter for the motion compensating processing based on condition 1 in this case also.

The color filter 202a_3 is described. When the illumination light is the white light, the Cy filter serves as the filter for the motion compensating processing based on condition 1. When the illumination light is the narrow band light, the Mg filter transmits only the light of the wavelength band $H_B$, so that this is substantially regarded as the B filter. Therefore, based on condition 1, the number of filters which transmit only the light of the wavelength band $H_B$ and the number of filters which transmit the cyan color component are the same. Then, condition 2 is applied and the Cy filter serves as the filter for the motion compensating processing when the illumination light is the narrow band light because the Cy filter has higher sensitivity than the B filter.

The color filter 202a_4 is described. When the illumination light is the white light, the Cy filter serves as the filter for the motion compensating processing based on condition 1. When the illumination light is the narrow band light, the W filter transmits the light of the wavelength band $H_B$ and the light of the wavelength band $H_G$, so that this is substantially regarded as the Cy filter. Therefore, the Cy filter (including the W filter) serves as the filter for the motion compensating processing also when the illumination light is the narrow band light.

The color filter 202a_5 is described. When the illumination light is the white light, the G filter serves as the filter for the motion compensating processing based on condition 1. When the illumination light is the narrow band light, the Mg filter transmits only the light of the wavelength band $H_B$, so that this is substantially regarded as the B filter. Therefore, based on condition 1, the number of substantial B filters and the number of G filters are the same. Then, condition 2 is applied and the B filter (including the Mg filter) serves as the filter for the motion compensating processing because the B filter has higher sensitivity than the G filter.

The color filter 202a_6 is described. When the illumination light is the white light, the W filter serves as the filter for the motion compensating processing based on condition 1. When the illumination light is the narrow band light, the W filter is substantially regarded as the Cy filter and the Mg filter is substantially regarded as the B filter. Therefore, based on condition 1, the number of filters which transmit the cyan color component and the number of filter which transmit only the light of the wavelength band $H_B$ are the same. Then, condition 2 is applied and the W filter which is substantially the Cy filter serves as the filter for the motion compensating processing because the Cy filter has higher sensitivity than the B filter.

In this manner, the motion compensating unit 411 specifies the filter which should be used in the motion compensating processing with reference to the type information of the illumination light and the used filter information T1 (scope ID) and performs the motion compensating processing of the images captured at different times by using the electric signal output by the pixel (pixel of interest) corresponding to the specified filter.

With reference to FIGS. 1 and 2 again, the configuration of the processor unit 4 is continuously described.

The input unit 46 being an interface for inputting to the endoscope device 1 by the user includes a power switch for turning on/off the power, a mode switching button for switching a shooting mode and various other modes, an illumination light switching button for switching the illumination light of the light source unit 3 and the like.

The control unit 47 controls driving of each component including the endoscope 2 and the light source unit 3 and controls input/output of information to/from each component. The control unit 47 outputs setting data for imaging control stored in the recording unit 45 (for example, the pixel to be read), a timing signal indicating imaging timing, an emitting timing signal indicating an emitting timing by the light source unit 3 and the like to the endoscope 2 and the light source unit 3 through a predetermined signal line and bus. The control unit 47 outputs the type information of the illumination light and the color filter information (identification information D) obtained through the imaging information storage unit 206 to the noise reducing unit 41.

Next, the display unit 5 is described.

The display unit 5 displays an image corresponding to a display image signal input from the processor unit 4. The display unit 5 is formed of a liquid crystal, organic EL (electro luminescence) or the like.

Figure 12:
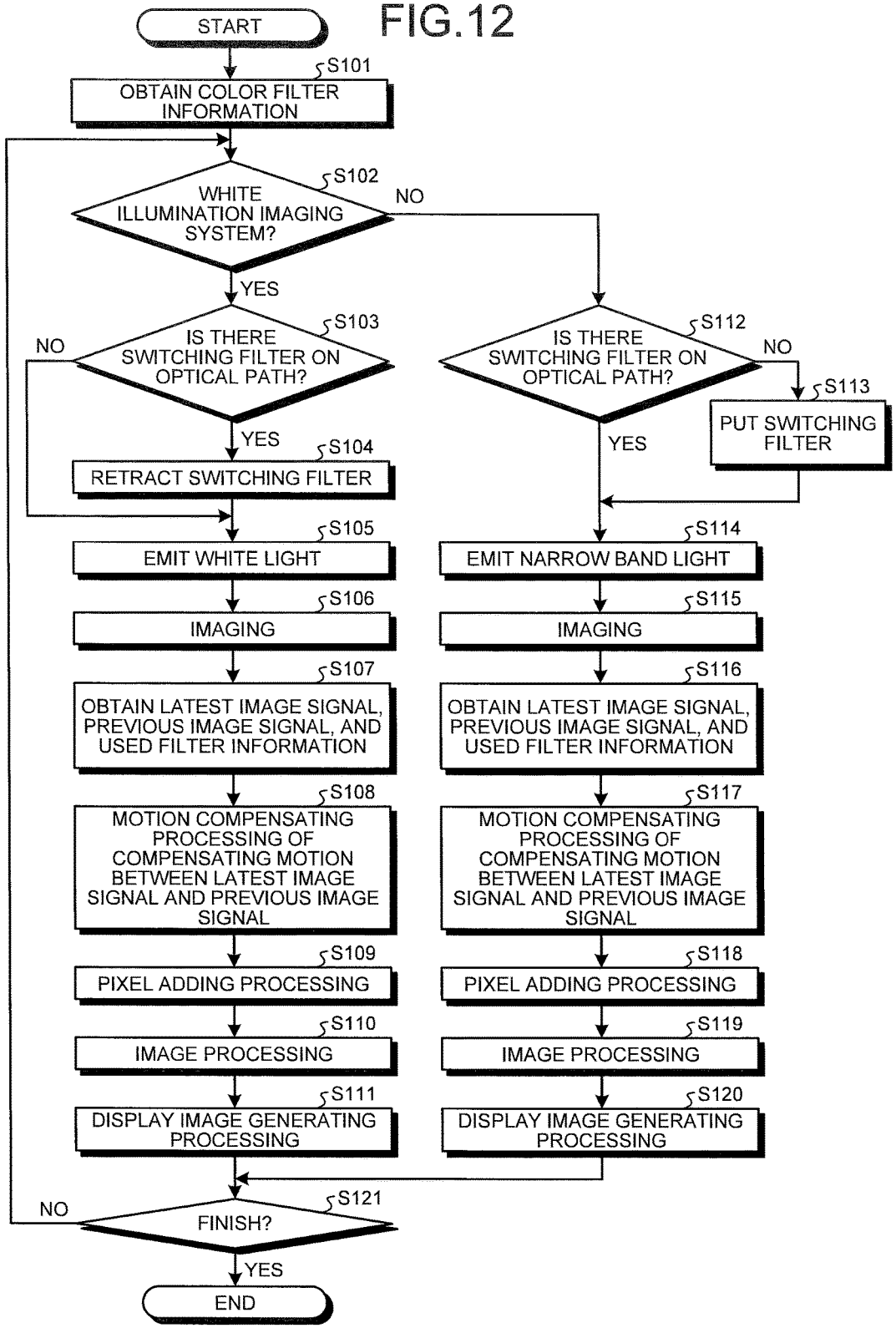
FIG. 12 is a flowchart illustrating an overview of a process executed by the endoscope device according to one embodiment of the present disclosure.

A process executed by the endoscope device 1 having the above-described configuration is described. FIG. 12 is a flowchart illustrating an overview of the process executed by the endoscope device 1. Meanwhile, an example of the color filter 202a_1 (filter unit U1) is described in the following process.

As illustrated in FIG. 12, the control unit 47 first obtains the color filter information (scope ID) from an identification information recording unit 206a of the imaging information storage unit 206 of the endoscope 2 connected to the processor unit 4 (step S101). In this case, the control unit 47 outputs the color filter information obtained from the identification information recording unit 206a to the motion compensating unit 411.

Subsequently, when the imaging system of the endoscope device 1 is the white illumination light imaging system (step S102: Yes), if the switching filter 31c is put on the optical path of the white light emitted by the light source 31a (step S103: Yes), the illumination control unit 32 retracts the switching filter 31c from the optical path of the light source 31a by controlling the driving unit 31d (step S104).

Thereafter, the illumination control unit 32 allows the light source 31a to emit the white light toward biological tissue in the subject (step S105). In this case, the illumination control unit 32 allows the light source 31a to continuously emit the white light until an instruction signal to give an instruction to finish examining the subject or the instruction signal to give an instruction to emit the narrow band illumination light is input from the operating unit 22. At that time, the illumination control unit 32 outputs the type information of the illumination light to the motion compensating unit 411 through the control unit 47.

Subsequently, the control unit 47 allows the imaging device 202 to image the biological tissue in the subject on which the light source unit 3 emits the white light (step S106).

Thereafter, the motion compensating unit 411 obtains the current frame corresponding to the image signal of the latest image generated by the imaging device 202 through the A/D converter 205, the previous frame corresponding to a previous image signal from which the noise component is reduced from the frame memory 42, and the used filter information from the used filter information recording unit 451 (step S107).

Subsequently, the motion compensating unit 411 executes the motion compensating processing to compensate the motion between the previous frame and the current frame based on the color filter information, the type information of the illumination light, and the used filter information input from the control unit 47 (step S108).

Figure 13:
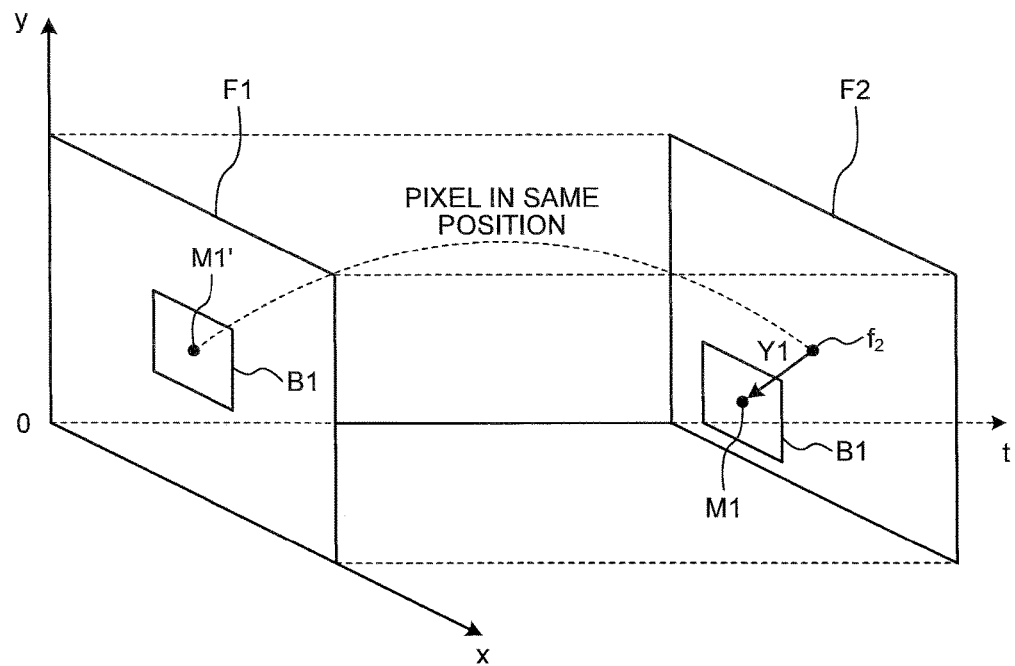
FIG. 13 is a view schematically illustrating motion compensation between images at different imaging timings performed by a motion compensating unit according to one embodiment of the present disclosure.

FIG. 13 is a view schematically illustrating a method of selecting the pixel used in the motion compensating processing executed by the motion compensating unit 411 on the previous frame and the current frame.

As illustrated in FIG. 13, the motion compensating unit 411 performs the motion compensating processing to compensate the motion between a previous frame F1 and a current frame F2 by using a block matching method on the previous frame F1 corresponding to the previous image signal. The block matching method detects a position in the current frame F2 to which a target pixel M1' of the previous frame F1 moves, for example. For this purpose, the motion compensating unit 411 makes a block B1 (small region) around the target pixel M1' a template and scans the current frame F2 by using the template of the block B1 around a pixel $f_2$ in the same position as the position of the target pixel M1' of the previous frame F1 in the current frame F2 to make a central pixel in a position in which a difference absolute value sum between the templates is the smallest a target pixel M1. That is to say, the motion compensating unit 411 detects a motion amount Y1 (motion vector) from the target pixel M1' to the target pixel M1 in the current frame F2 and performs the process on all the pixels of the previous frame F1.

Figure 14:
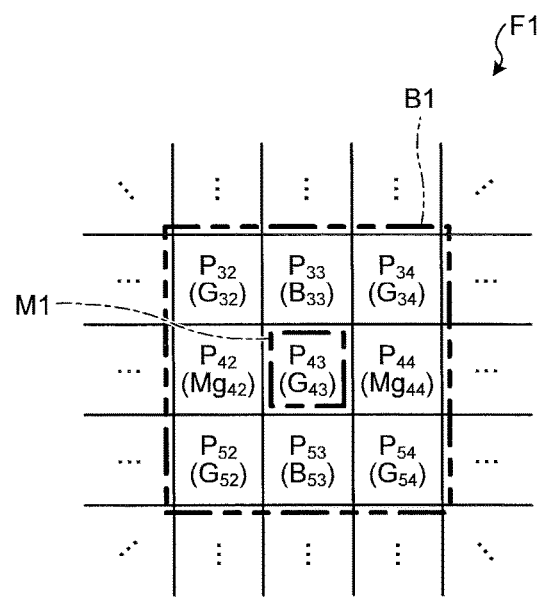
FIG. 14 is a view schematically illustrating a pixel of interest and a block used in motion compensating processing performed by the motion compensating unit according to one embodiment of the present disclosure.

Under conditions illustrated in FIG. 13, the motion compensating unit 411 selects the pixel of interest based on the color filter information, the type information of the illumination light, and the used filter information. Specifically, as illustrated in FIG. 14, when the color filter 202a is the color filter 202a_1 (filter unit U1) and the illumination light is the white light, if the target pixel M1 is the pixel of interest and a pixel $P_{43}$, the motion compensating unit 411 scans the previous frame F1 for the pixel of interest by using the block B1 formed of the pixels adjacent to the pixel $P_{43}$ around the pixel $P_{43}$ the template according to the used filter information. Meanwhile, in FIG. 14, the filter corresponding to the pixel $R_{ij}$ is described in parentheses.

Figure 15:
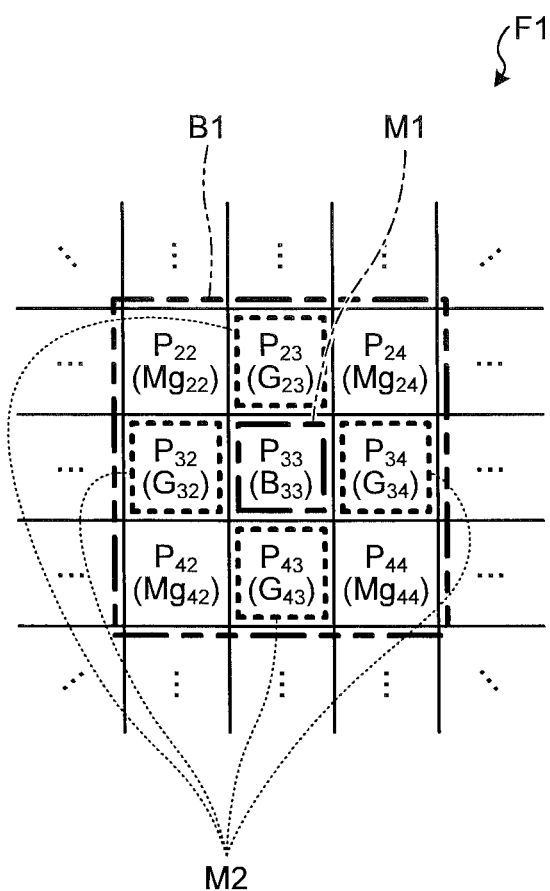
FIG. 15 is a view schematically illustrating another pixel of interest and another block used in the motion compensating processing performed by the motion compensating unit according to one embodiment of the present disclosure.

In contrast, as illustrated in FIG. 15, when the color filter 202a is the color filter 202a_1 (filter unit U1) and the illumination light is the white light, if the target pixel M1 is not the pixel of interest but a pixel $P_{33}$, the motion compensating unit 411 scans the previous frame F1 by using the block B1 formed of pixels $P_{23}$, $P_{32}$, $P_{34}$, and $P_{43}$ around the pixel $P_{33}$ being the pixels of interest in place of the pixel $P_{33}$ as the template according to the used filter information. According to this, the motion compensation according to a characteristic of the illumination light may be performed, so that the motion amount Y1 generated between the previous frame F1 and the current frame F2 may be correctly detected.

With reference to FIG. 12 again, steps after step S109 are continuously described.

At step S109, the pixel adding unit 412 performs pixel adding processing to add the pixel value of each pixel of the current frame (latest image) corresponding to the latest image signal on which the motion compensating unit 411 performs the motion compensation to the pixel value of each pixel of the current frame (latest image) corresponding to the latest image signal or takes an average of them to output to the image processing unit 43.

Subsequently, the image processing unit 43 performs the image processing of performing the demosaicing processing, color component generating processing, the color image generating processing and the like on the image signal input from the noise reducing unit 41 to output to the display image generating unit 44 (step S110).

Thereafter, the display image generating unit 44 performs display image generating processing of generating the display image signal for display on the image signal input from the image processing unit 43 to output to the display unit 5 (step S111). After step S111, the endoscope device 1 shifts to step S121 to be described later.

At step S103, when the switching filter 31c is not put on the optical path of the white light emitted by the light source 31a (step S103: No), the endoscope device 1 shifts to step S105.

Next, a case in which the imaging system of the endoscope device 1 is not the white illumination light imaging system, that is to say, the narrow band imaging at step S102 (step S102: No) is described. In this case, when the switching filter 31c is put on the optical path of the white light emitted by the light source 31a (step S112: Yes), the illumination control unit 32 allows the illuminating unit 31 to emit the narrow band light to the biological tissue in the subject (step S114). At that time, the illumination control unit 32 allows the light source 31a to continuously emit the white light until the instruction signal to give an instruction to finish examining the subject or the instruction signal to give an instruction to emit the narrow band illumination light is input from the operating unit 22. Furthermore, the illumination control unit 32 outputs the type information of the illumination light to the motion compensating unit 411 through the control unit 47.

Subsequently, the control unit 47 allows the imaging device 202 to image the biological tissue in the subject irradiated with the narrow band light emitted by the illuminating unit 31 (step S115).

Thereafter, the motion compensating unit 411 obtains the current frame corresponding to the latest image signal generated by the imaging device 202 through the A/D converter 205, the previous frame corresponding to the previous image signal from which the noise component is reduced from the frame memory 42, and the used filter information from the used filter information recording unit 451 (step S116).

Subsequently, the motion compensating unit 411 executes the motion compensating processing to compensate the motion between the previous image signal and the latest image signal based on the used filter information obtained from the used filter information recording unit 451 (step S117).

Thereafter, the pixel adding unit 412 performs the pixel adding processing to add the pixel value of each pixel of the current frame corresponding to the latest image signal on which the motion compensating unit 411 performs the motion compensation to the pixel value of each pixel of the current frame corresponding to the latest image signal to output to the image processing unit 43 (step S118).

Subsequently, the image processing unit 43 performs the image processing of performing the demosaicing processing, the color component generating processing, the color image generating processing and the like on the image signal input from the noise reducing unit 41 to output to the display image generating unit 44 (step S119).

Thereafter, the display image generating unit 44 performs the display image generating processing of allocating the pixel value of the B pixel and a component of the capillary input from the image processing unit 43 to a B channel and a G channel of the display unit 5 and allocating a component of a deep blood vessel to an R channel to output to the display unit 5 (step S120). According to this, a site of the capillary on a surface is colored to reddish-blown and other sites are colored to cyan to green and an emphasized image in which the capillary on the mucous membrane surface is emphasized is displayed on the display unit 5. After step S120, the endoscope device 1 shifts to step S121.

After step S111 or step S120, when the instruction signal to finish examining the subject is input through the operating unit 22 (step S121: Yes), the endoscope device 1 finishes this process. In this case, the illumination control unit 32 stops the light source 31a. On the other hand, when the instruction signal to finish examining the subject is not input through the operating unit 22 (step S121: No), the endoscope device 1 returns to step S102.

When the switching filter 31c is not put on the optical path of the white light emitted by the light source 31a at step S112 (step S112: No), the illumination control unit 32 controls the driving unit 31d to put the switching filter 31c on the optical path of the light source 31a (step S113). After step S113, the endoscope device 1 shifts to step S114.

According to one embodiment described above, it is possible to appropriately reduce the noise component in both the white illumination light imaging system and the narrow band imaging system.

Meanwhile, although the endoscope device 1 according to the above-described embodiment is described to switch the illumination light emitted by the illuminating unit 31 between the white illumination light and the narrow band illumination light by putting/removing the switching filter 31c regarding the white light emitted from one light source 31a, it is also possible to switch two light sources which emit the white illumination light and the narrow band illumination light to emit any one of the white illumination light and the narrow band illumination light. When the two light sources are switched to emit any one of the white illumination light and the narrow band illumination light, it is also possible to apply to a capsule endoscope introduced into the subject provided with the light source unit, the color filter, and the imaging device, for example.

Any color filter in which the number of filters which transmit the light of the wavelength band $H_G$ is equal to or larger than half the number of filters which form the filter unit and the number of filters which transmit the light of the wavelength band $H_B$ is equal to or larger than the number of filters which transmit the light of the wavelength band $H_G$ in the filter unit may serve as the color filter according to the present disclosure; arrangement satisfying the above-described condition is also applicable in addition to the above-described arrangement.

Although it is described that the color filter including a plurality of transmitting filters each of which transmits the light of a predetermined wavelength band is provided on the light receiving surface of the imaging device in the present disclosure, each transmitting filter may also be individually provided on each pixel of the imaging device.

The endoscope device according to the present disclosure may also be applied to an ultrasound endoscope in which the imaging device and an ultrasound transducer are embedded in the distal end thereof and the capsule endoscope which may be introduced into the subject. When this is applied to the capsule endoscope, if the two light sources are switched to emit any one of the white illumination light and the narrow band illumination light, the light source unit, the color filter, and the imaging device may be provided in a casing of the capsule, for example.

Meanwhile, in the description of the flowchart in this specification, although anteroposterior relation of the processes between the steps is specified by using representations such as "first", "thereafter", and "subsequently", order of the processes required for carrying out the present disclosure is not uniquely determined by the representations. That is to say, the order of processes in the flowchart described in this specification may be changed without contradiction.

The endoscope device according to the present disclosure has an effect of appropriately reducing the noise component in both the white illumination light imaging system and the narrow band imaging system.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope device comprising:
    a light source unit configured to emit white illumination light including light of red, green and blue wavelength bands or narrow band illumination light formed of narrow band light included in each of the blue and green wavelength bands;
    an imaging device configured to perform photoelectric conversion on light received by a plurality of pixels arranged in a lattice pattern to generate an electric signal as an image signal;
    a color filter comprising a plurality of filter units,
        wherein each of the filter units is comprised of a predetermined total number of pixel filters arranged corresponding to the plurality of pixels, the pixel filters comprising green light transmittable pixel filters and blue light transmittable pixel filters, so that:
            the number of the green light transmittable pixel filters is more than or equal to half the predetermined total number of the pixel filters, and
            the number of the blue light transmittable pixel filters is more than or equal to the number of the green light transmittable pixel filters,
        wherein the green light transmittable pixel filters are either or both of a green pixel filter configured to transmit the light of the green wavelength band and a pixel filter configured to transmit at least the light of the blue wavelength band and the light of the green wavelength band, and
        wherein the blue light transmittable pixel filters are any one of a blue pixel filter configured to transmit the light of the blue wavelength band, the pixel filter configured to transmit at least the light of the blue wavelength band and the light of the green wavelength band, and a pixel filter configured to transmit at least the light of the blue wavelength band and the light of the red wavelength band; and
    a processor comprising hardware, wherein the processor is configured to:

select a pixel of interest, based on the light emitted by the light source unit and an arrangement of the pixel filters in each of the filter unit of the color filter; and detect motion between images captured at different times by using the electric signal output by the pixel of interest, such that a noise component included in the image signal is reduced.

2. The endoscope device according to claim 1,
wherein the processor is configured to select the pixel of interest based on following conditions:

condition 1: the pixel filter of the greatest number which transmits the same type of color component in the filter unit is selected; and condition 2: when there is a plurality of pixel filters satisfying condition 1, the pixel filter having higher sensitivity to the narrow band illumination light is selected.

3. The endoscope device according to claim 1,
wherein the processor is configured to refer to a memory storing a relationship between the pixel of interest and the light emitted by the light source unit and the arrangement of the pixel filters in each of the filter unit of the color filter to select the pixel of interest.

* * * * *